United States Patent
Bagaoisan et al.

[11] Patent Number: 5,868,705
[45] Date of Patent: Feb. 9, 1999

[54] PRE-STRETCHED CATHETER BALLOON

[76] Inventors: Celso J. Bagaoisan, 4441 Pomponi St., Union City, Calif. 94587; Ketan P. Muni, 97 Frontier Trail Dr., San Jose, Calif. 95136; Hung V. Ha, 2359 Denair Ave., San Jose, Calif. 95122; Sivette Lam, 609 Capital Ave. #143, San Jose, Calif. 95133; Gholan-Reza Zadno-Azizi, 8213 Del Monte Ave., Newark, Calif. 94560

[21] Appl. No.: 812,140

[22] Filed: Mar. 6, 1997

Related U.S. Application Data

[63] Continuation-in-part of Ser. No. 650,464, May 20, 1996, abandoned.

[51] Int. Cl.⁶ .................................................. A61M 29/00
[52] U.S. Cl. .............................. 604/96; 606/194; 264/532
[58] Field of Search ................................ 604/96, 97, 98, 604/101; 606/191–194; 264/530, 532, 573, 523, 540

[56] References Cited

U.S. PATENT DOCUMENTS

| | | |
|---|---|---|
| 3,144,868 | 8/1964 | Jascalevich . |
| 4,386,179 | 5/1983 | Sterling . |
| 4,445,892 | 5/1984 | Hussein et al. . |
| 4,468,216 | 8/1984 | Muto . |
| 4,511,354 | 4/1985 | Sterling . |
| 4,573,966 | 3/1986 | Weikl et al. . |
| 4,698,059 | 10/1987 | Johnson .............................. 604/200 X |
| 4,886,496 | 12/1989 | Conoscenti et al. . |
| 4,906,244 | 3/1990 | Pinchuk et al. . |
| 4,946,466 | 8/1990 | Pinchuk et al. . |
| 4,964,409 | 10/1990 | Tremulis . |
| 5,059,178 | 10/1991 | Ya . |
| 5,163,906 | 11/1992 | Ahmadi . |
| 5,167,239 | 12/1992 | Cohen et al. . |
| 5,322,508 | 6/1994 | Viera . |
| 5,423,742 | 6/1995 | Theron . |
| 5,439,000 | 8/1995 | Gunderson et al. . |
| 5,449,343 | 9/1995 | Samson et al. . |
| 5,462,529 | 10/1995 | Simpson et al. . |
| 5,490,838 | 2/1996 | Miller . |
| 5,500,180 | 3/1996 | Anderson et al. . |
| 5,556,383 | 9/1996 | Wang et al. . |
| 5,558,644 | 9/1996 | Boyd et al. .............................. 604/96 |

FOREIGN PATENT DOCUMENTS

| | | |
|---|---|---|
| 0 531 117 A2 | 3/1993 | European Pat. Off. . |
| 0 577 009 A1 | 1/1994 | European Pat. Off. . |
| 0 592 885 A2 | 4/1994 | European Pat. Off. . |
| 0 795 340 A2 | 3/1997 | European Pat. Off. . |
| WO 95/23619 | 3/1994 | WIPO . |
| WO 96/12516 | 5/1996 | WIPO . |
| WO 96/15824 | 5/1996 | WIPO . |
| WO 98/03218 | 7/1997 | WIPO . |

OTHER PUBLICATIONS

R. Carew, E. Perrin, D. Deisler and E.P. Goldberg. "The Torch". The Newsletter of the Society For Biomaterials, vol. 10, No. 4.

*Primary Examiner*—Mark Bockelman
*Assistant Examiner*—N. Kent Gring

[57] ABSTRACT

Disclosed herein is a compliant catheter balloon with an improved elastic response and reduced longitudinal expansion, and a method of forming the same. The balloon comprises a SEBS block copolymer, which is longitudinally prestretched during the balloon manufacture process.

19 Claims, 1 Drawing Sheet

PRE-STRETCHED CATHETER BALLOON

CROSS-REFERENCE TO RELATED APPLICATION

The present application is a continuation-in-part of application Ser. No. 08/650,464 filed on May 20, 1996 now abandoned, the entirety of which is incorporated by reference.

BACKGROUND OF THE INVENTION

The present invention generally relates to medical devices, and in particular, to improved compliant expansion balloons for use with medical catheters.

Compliant inflatable balloons, of the type used with medical catheters, increase in diameter with increasing inflation pressure until the balloon burst pressure is reached, as is well-known to those of skill in the art. Such balloons are especially advantageous when used as an occlusion balloon, or as the securing element of an anchorable guidewire. In both applications, the balloon must be expanded to contact the blood vessel wall. In some treatment procedures, however, the clinician does not know the precise diameter of the blood vessel segment that the balloon must contact. In these situations, the compliant expansion profile of the balloon permits the clinician to make the required contact, by application of increasing inflation pressures to cause increased balloon radial expansion until contact is achieved.

Conventional compliant expansion balloons are generally made of elastomeric materials, such as latex and silicone. Balloons made of these materials utilizing conventional balloon formation techniques suffer from several disadvantages which adversely affect the balloon's performance.

One disadvantage of conventional compliant balloons relates to their elastic response. It is desirable for catheter balloons to have a predictable inflation profile. That is, the balloon should inflate to a certain known size upon application of a specific pressure. Moreover, the balloon should exhibit good elasticity, inflating to approximately the same size upon application of the same specific pressure or volume, even after the balloon has been inflated and deflated multiple times. However, conventional compliant balloons often do not exhibit this desired elastic response, and tend to inflate to larger sizes upon application of the same specific pressure each subsequent time they are inflated. This is because each inflation stretches the balloon, and upon deflation, the balloon does not return to its original deflated size, but instead is somewhat larger. Consequently, upon each subsequent inflation, the stretched balloon inflates to a larger size than before, making it difficult for the clinician to predict the amount of pressure that must be applied to inflate the balloon to the size needed to contact the vessel.

Another disadvantage of conventional compliant balloons relates to their longitudinal expansion. As described previously, compliant balloons tend to increase in radial diameter with increasing inflation pressure. In addition, many compliant expansion balloons also tend to increase in length with increasing inflation pressure. This is an undesirable expansion characteristic, as it creates an unwanted shearing force within the blood vessel, which could lead to vessel trauma.

Accordingly, there exists a need for compliant expansion balloons for use as occlusion balloons on catheters, or as securing members on anchorable guidewires, which have a predictable elastic response, a predictable longitudinal expansion, and a predictable diameter, at different volumes or pressures. In addition, there is a need for methods of making such balloons.

SUMMARY OF THE INVENTION

The present invention advantageously provides a compliant expansion balloons with an improved elastic response and reduced longitudinal expansion. In one aspect of the present invention, there is provided a longitudinally pre-stretched styrene-ethylene-butylene-styrene (SEBS) compliant catheter balloon. Preferably, the balloon is formed in part by longitudinally stretching an extruded styrene-ethylene-butylene-styrene tube such that the tube increases in length by at least 200%. More preferably, the tube increases in length by at least 600 to 900%. It is also preferred that the balloon be formed from a tube stretched at a rate of from about 10 cm/min to about 30 cm/min. Balloons of this type exhibit decreased longitudinal expansion when inflated. Preferably, the longitudinal expansion of the balloon formed in part by stretching the extruded tube is 20%–50% less than a balloon formed from an unstretched tube of identical composition.

In another aspect of the present invention, there is provided a method of making a compliant inflatable catheter balloon with reduced longitudinal expansion. The first step of the method is to provide an extruded SEBS tube having a first length and a first inner diameter. The extruded SEBS tube is then stretched longitudinally so that the tube forms a second inner diameter smaller than the first diameter, and a second length greater than the first length.

In alternate first step, there is provided an extruded SEBS tube having a first length and a first thickness. The extruded SEBS tube is then stretched longitudinally so that the tube has a second length greater than the first length, and a second thickness which is less than the first thickness.

After the stretching process, the tube is preferably cut within two hours of the stretching step. In a preferred practice of the method, the second length is at least 600% greater than the first length, more preferably is at least 700% greater than the first length, and optimally is at least 900% greater than the first length.

In addition, it is also preferred that the second diameter be about 40% smaller than the first diameter, more preferably about 30% smaller than the first diameter.

The longitudinal stretching also preferably occurs at a rate of about 10 cm/min–30 cm/min, and takes place in an environment having a temperature of between 0° and 90° C.

DETAILED DESCRIPTION OF THE PREFERRED EMBODIMENT

Figure 1:
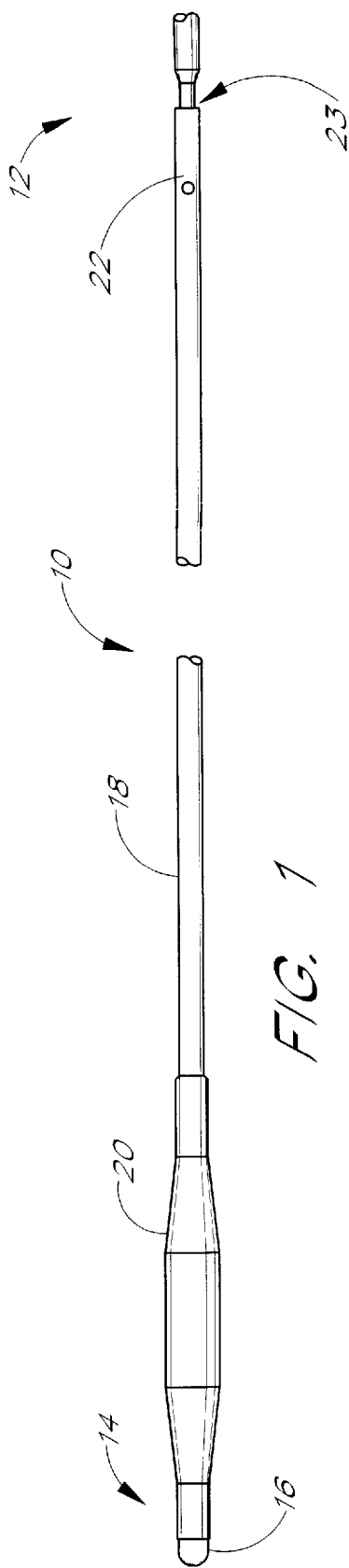
FIG. 1 is a side view of a catheter incorporating the pre-stretched balloon of the present invention.

Referring to FIG. 1, there is depicted a catheter 10 incorporating the balloon of the present invention. Although the balloon of the present invention is depicted and discussed in the context of being mounted on a simple occlusion balloon catheter having a single lumen, it should be appreciated that the present invention is applicable to more complex catheters having structures and functionalities not discussed herein. For example, the present inventors contemplate that the balloon of the present invention may be used on catheters having two or more lumen, such as the main catheter of an emboli containment system. In addition, the balloon of the present invention can be used as the securing member for an anchorable guide wire. The manner of adapting the balloon of the present invention to these various structures and functionalities will become readily apparent to those of skill in the art in view of the description which follows.

In the embodiment illustrated in FIG. 1, the balloon of the present invention is mounted on an occlusion balloon catheter 10. Catheter 10 generally comprises an elongate flexible tubular body 18 extending between a proximal control end 12 and a distal functional end 14. Tubular body 18 has a central lumen 40 (not shown) which extends between ends 12 and 14. An inflation port 22 is provided on tubular body 18 near the proximal end. Inflation port 22 is in fluid communication with lumen 40, such that fluid passing through inflation port 22 into or out of lumen 40 may be used to inflate or deflate inflatable balloons in communication with lumen 40. Lumen 40 is sealed fluid tight at distal end 14 in this embodiment.

The length of tubular body 18 may be varied considerably depending upon the desired application. For example, where catheter 10 serves as a guidewire for other catheters in a conventional percutaneous transluminal coronary angioplasty procedure involving femoral artery access, tubular body 18 is comprised of hollow hypotube having a length in the range of from about 160 to about 320 centimeters are preferred, with a length of about 180 centimeters being optimal for a single operator device and 300 centimeters for over the wire applications. Alternately, for a different treatment procedure, not requiring as long a length of tubular body 18, shorter lengths of tubular body 18 may be provided.

Tubular body 18 generally has circular cross-sectional configuration with an outer diameter within the range of from about 0.008 inches to 0.14 inches. Optimally, in most applications where catheter 10 is to be used as a guidewire for other catheters, the outer diameter of tubular body 18 ranges from 0.010 inches to 0.038 inches, and preferably is 0.038 inches in outer diameter or smaller. Larger or smaller sizes of tubular body 18 may also be used. Noncircular cross-sectional configurations of lumen 40 can also be adapted for use with the balloon of the present invention. For example, triangular cross-sectional configurations, rectangular, oval, and other noncircular cross-sectional configurations are also easily incorporated for use with present invention, as will be appreciated by those of skill in the art.

Tubular body 18 has sufficient structural integrity, or "pushability," to permit catheter 10 to be advanced through vasculature to distal arterial locations without buckling or undesirable kinking of tubular body 18. It is also desirable for tubular body 18 to have the ability to transmit torque, such as in those embodiments where it may be desirable to rotate tubular body 18 after insertion into a patient. A variety of biocompatible materials, known by those of skill in the art to possess these properties and to be suitable for catheter manufacture, may be used to fashion tubular body 18. For example, tubular body 18 may be made of stainless steel, or may be made of polymeric materials such as nylon, polyamide and polyimide or polyethylene or combinations thereof. In one preferred embodiment, the desired properties of structural integrity and torque transmission are achieved by forming tubular body 18 out of an alloy of titanium and nickel, commonly referred to as nitinol. In a more preferred embodiment, the nitinol alloy used to form tubular body 18 is comprised of about 50.8% nickel with the balance being titanium, which is sold under the trade name Tinel (TM) by Memry Corp. It has been found that a catheter tubular body having this composition of nickel and titanium exhibits an improved combination of flexibility and kink resistance in comparison to other materials. Further details are disclosed in our co-pending application entitled HOLLOW MEDICAL WIRES AND METHODS FOR CONSTRUCTING SAME, application Ser. No. 08/812,876, filed Mar. 6, 1997 the entirety of which is incorporated by reference.

For the embodiment illustrated in FIG. 1, an inflatable balloon 20 of the present invention is mounted near distal end 14. Inflatable balloon 20 is in fluid communication with lumen 40 via a fill hole (not shown) extending through tubular body 18 within balloon 20. Accordingly, balloon 20 may be inflated or deflated by the passage of fluid through port 22.

Balloons of the present invention, such as balloon 20, are formed out of material comprising a block copolymer of styrene-ethylene-butylene-styrene (SEBS). It has been found that SEBS resins can be used to form catheter balloons with improved elasticity in comparison to other compliant balloon materials. Preferred SEBS resins for manufacture of balloons of the present invention may be purchased under the trade name C-FLEX, sold by Consolidated Polymer Technologies. In particular, the C-FLEX (TM) resin grade R70-050-000 has proven especially preferable for manufacture of balloons of the present invention.

As a first step in the balloon formation process, the selected SEBS resin is extruded to form a tube which will subsequently be shaped into a balloon of the present invention. The resin may be extruded to form tubes having a variety of different internal and outer diameters, as can be readily appreciated by those of skill in the art. It is preferable, however, that the inner diameter of the extruded tubing be no more than about 120% greater and preferably no more than about 80% greater than the outer diameter of the catheter tubular body to which the finished balloon will be mounted. For example, where the outer diameter of tubular body 18 is about 0.014 inches, as is preferable for many hollow guidewire applications, the inner diameter of this extruded SEBS tubing is preferably from about 0.016 inches to about 0.030, more preferably 0.020 inches to about 0.027 inches, and optimally about 0.025 inches. The outer diameter of the extruded SEBS tube is preferably about 0.035 inches to about 0.060 inches, more preferably 0.042 inches to about 0.058 inches, and optimally is 0.053 inches (For a 3.5–4.5 mm balloon). Other balloon sizes will tend to require different dimensional parameters.

Any suitable one inch extrusion apparatus may be used to form the extruded SEBS tubes. For example, balloons of the present invention may be formed from tubing extruded on a 1" Harrel extruder, set to a draw down ratio of from about 1 to about 1.4, more preferably to a draw down ratio of about 1 to about 1.2.

It is important to monitor the extrusion process to ensure that the resulting tubing has substantially uniform inner and outer diameters along its length. In other words, uniform concentricity of the resulting extruded tube is very important. One important variable that needs to be monitored and controlled is the amount of tension which is applied to the tubing during the extrusion process. It is important not to apply too much tension, so that the tubing keeps proper dimensions along its length. For example, for extrusion of tubing having an inner diameter of about 0.025 inches and an outer diameter of about 0.053 inches, applied tension during extension preferably does not exceed 4 oz.

Extrusion tension can be controlled by a variety of means, as is known to those of skill in the art. For example, extrusion tension can be controlled by using hand extrusion, by low tension pullers, by low tension winders, or by other means known to those of skill in the art.

The extruded SEBS tubing has an inner diameter much larger than the outer diameter of the catheter tubular body, such that the tubing may not be directly mounted to the tubular body to form a balloon. Accordingly, the inner diameter of the SEBS tubing must be reduced before the SEBS tube may be mounted to the catheter tubular body as a balloon.

Thus, one important step in forming balloons of the present invention involves reducing both the inner and outer diameter of the SEBS tubes by a pre-stretching process. Advantageously, the pre-stretching process not only reduces the inner and outer diameters such that the SEBS tubing may be mounted to a catheter tubular body as a balloon, but also results in a finished compliant balloon which exhibits reduced longitudinal expansion upon inflation. Indeed, it has been discovered that the pre-stretching process of the present invention is capable of reducing longitudinal expansion of finished SEBS balloons by from about 20% to about 50%.

The pre-stretching process generally comprises longitudinally stretching the extruded SEBS tube by at least 200%, such that substantially all lengthwise deformation of the SEBS tube occurs along a line parallel to the longitudinal axis of the SEBS tube. In other words, the tube is stretched lengthwise while controlling the stretching process variables to minimize curvature or other bends in the tube. Preferably, the extruded SEBS tube is stretched by at least 400%, more preferably by at least 600%, and optimally by at least 900%, such that the inner diameter of the SEBS tube decreases from its starting size to about 0.002–0.003 inches greater than the outer diameter of the catheter tubular body to which the extruded tube is to be mounted as a balloon. Furthermore, the pre-stretching process also preferably reduces the outer diameter of the SEBS tube from its starting size, to an outer diameter which is at least 15% smaller, more preferably 25% smaller, and optimally at least 30% smaller than the starting outer diameter size. For example, where the starting inner diameter of an extruded SEBS tube is about 0.025 inches, and the starting outer diameter of the tube is 0.053 inches, the tube may be stretched so that it length increases by about 600–700%, so that the resulting inner diameter of the tube is about 0.016 inches and the resulting outer diameter is about 0.035 inches. A stretched tube with these dimensions is preferably mounted to the embodiment of the tubular body 18 having an outer diameter of about 0.014 inches to form a balloon.

As is readily appreciated by those of skill in the art, where the outer diameter of the tube is reduced more than the inner diameter, the thickness of the tube also decreases. Preferably the thickness is reduced by at least 10%, more preferably by at least 20%, and optimally by at least 30%. Greater reductions in thickness may also result from the pre-stretching process and still function in accordance with the present invention, depending upon the grade of SEBS resin and the stretching conditions used. The manner of adapting these different resin grades and stretching conditions will be apparent to those of skill in the art in view of the description herein.

The pre-stretching process is preferably carried out at temperature which facilitates the stretching without contributing to any undesirable bending of the tube. For most grades of SEBS, temperatures of between 0° to about 90° C. are preferred. Temperatures lower than this generally require the application of increased longitudinal force to carry out the stretching process, resulting in increased risk of nonuniform stretching or bending of the resulting tube. Moreover, at temperatures greater than about 90° C., the SEBS block copolymer used to form the tubing tends to soften considerably, such that gravitational force may introduce unwanted bend or curvature in the tube. Optimally, stretching is done at about 25°–30° C.

The stretching rate also has an important effect on the properties of the resulting balloon. Preferably, the SEBS tubing is stretched at a rate of from about 0.5 cm per min to about 50 cm per minute, more preferably at a rate of less than 30 cm/min., and optimally is stretched at a rate of 10 cm inches per minute at room temperature. Stretching rates greater than the maximum amount may result in undesirable residual elongation. After the pre-stretching process is completed, the stretched SEBS tubing is preferably permitted to settle for a period of about 10–15 seconds, prior to removal from the stretching apparatus.

Once the pre-stretching process is completed, the stretched tubing is preferably cut to appropriate balloon length within two hours of the stretching, otherwise tube relaxation may occur which adversely affects the dimensions of the stretched tube. Cutting may be performed by any means known to those of skill in the art. One preferred cutting process comprises inserting a stainless steel mandrel into a polyimide tube, and then inserting the mandrel/polyimide tube combination into the lumen of the stretched SEBS tube. The stainless steel mandrel is then removed, leaving the polyimide tube within the stretched SEBS tube. The polyimide tube provides structural support to the SEBS tube during the cutting process, facilitating the formation of straight cut edges. For example, for a stretched SEBS tube having an inner diameter of about 0.016 inches and an outer diameter of about 0.035 inches, a stainless steel mandrel having an outer diameter of 0.013 inches is inserted into a polyimide tube having an inner diameter of 0.0145 inches and an outer diameter of 0.0155 inches. The combination is then inserted into the stretched SEBS tube, and the stainless steel mandrel is removed. A standard cutting tool, such as a razor blade is then used to cut through the SEBS tubing and the polyimide tubing into segments having lengths of approximately 9 mm. After the cutting is completed, the polyimide tubing is removed.

The stretched and cut pieces of SEBS tubing may then be bonded to catheter tubular bodies to form compliant inflatable balloons. Conventional balloon bonding techniques may be used to mount the SEBS balloons to catheter tubular bodies. Such techniques include adhesive bonding and heat bonding, as known to those of skill in the art. In one preferred embodiment where the catheter tubular body comprises nitinol, a primer is first applied to the inner surface of each end of the SEBS tube to improve the bonding of the SEBS tube to nitinol. One suitable primer found useful for the priming step is 7701 LOCTITE, sold by Loctite Corp. However, as will be appreciated by those of skill in the art, other primers may also be used. The primer is preferably applied only to the inner surface of the SEBS tube at its ends, and more preferably, each end inner surface is primed for a distance of about 2 mm extending inward.

After the priming step, the primed tubing is slid over the catheter tubular body to the appropriate balloon position, such as over a fill hole in communication with an inflation lumen. Each end of the SEBS tubing is then mounted to the catheter tubular body to form a fluid tight seal. In a preferred embodiment, a cyanoacrylate adhesive is used to bond the SEBS tubing to the nitinol catheter tubular body. One preferred cyanoacrylate is LOCTITE 4011, sold by Loctite Corp. When using the LOCTITE 4011 adhesive, however, it is important to control the humidity of the surrounding environment, such that the humidity is maintained at at least 35% to 40%.

While adhesive bonding is taking place, clamps are preferably placed adjacent to the working area of the balloon to prevent adhesive flow inward. For example, if a 9 mm SEBS tube is bonded to a catheter tubular body along 2 mm at each end, clamps are placed slightly inward of the 2 mm mark, so that 5 mm of tubing is not bonded to the tubular body, and may function as a balloon.

After the SEBS tube has been bonded to the catheter tubular body to form a balloon, and the adhesive has set, tapers are preferably formed on the balloon to facilitate unhindered movement within a patient. Tapers may be added by conventional means known to those of skill in the art, such as adhesive bonding of the tapered parts separately to the catheter after the balloon has been attached. Alternately, tapers can be formed by adhesives which are applied to the balloon. In addition, it is possible to mold the balloon with a taper and then attach it.

It will be appreciated that certain variations of the present invention may suggest themselves to those skilled in the art. The foregoing detailed description is to be clearly understood as given by way of illustration, the spirit and scope of this invention being limited solely by the appended claims.

What is claimed is:

1. A compliant catheter balloon formed in part by longitudinly stretching an extruded styrene-ethylene-butylene-styrene (SEBS) tube at a forming temperature between about 0° and 90° C. such that the tube increases in length by at least 200%, wherein the stretching of the tube reduces the longitudinal expansion of the balloon by at least about 20% upon inflation compared to a balloon formed from an unstretched tube of identical composition.

2. The balloon of claim 1, wherein the tube increases in length by at least 400%.

3. The balloon of claim 1, further comprising stretching the tube at a rate of less than 30 cm/min.

4. The balloon of claim 2, wherein the longitudinal expansion of the balloon formed in part by stretching the extruded tube is at least 20% less than a balloon formed from an unstretched tube of identical composition.

5. A method of making a compliant inflatable catheter balloon with reduced longitudinal expansion comprising the steps of:
   providing an extruded SEBS tube having a first length and a first inner diameter;
   stretching the extruded SEBS tube longitudinally at a forming temperature between about 0° and 90° C. so that the tube forms a second inner diameter smaller than the first diameter, and a second length greater than the first length.

6. The method of claim 5, further comprising cutting the stretched SEBS tube within two hours of the stretching step.

7. The method of claim 5, wherein the second length is at least 200% greater than the first length.

8. The method of claim 7, wherein the stretched second length is at least 400% greater than the first length.

9. The method of claim 8, wherein the stretched second length is at least 600% greater than the first length.

10. The method of claim 5, wherein the second diameter is 10% smaller than the first diameter.

11. The method of claim 10, wherein the second diameter is 40% smaller than the first diameter.

12. The method of claim 5, wherein the longitudinal stretching occurs at a rate of about 10 cm/min.

13. The method of claim 5, wherein the stretching takes place at a temperature of between about 25° and 30° C.

14. The method of claim 5, wherein the extruded SEBS tube has a first wall thickness prior to the stretching step, and a second wall thickness after the stretching step, and the first wall thickness is greater than the second wall thickness.

15. The method of claim 14, wherein the first wall thickness is at least 10% greater than the second wall thickness.

16. The method of claim 15, wherein the first wall thickness is at least 30% greater than the second wall thickness.

17. A longitudinally pre-stretched SEBS compliant catheter balloon.

18. A method of making a compliant inflatable catheter balloon with reduced longitudinal expansion comprising the steps of:
   extruding a styrene-ethylene-butylene-styrene (SEBS) resin to form a tube having a first length and a first inner diameter;
   stretching the extruded tube longitudinally so that the tube forms a second inner diameter smaller than the first diameter, and a second length greater than the first length, wherein the stretching of the tube reduces the longitudinal expansion of the balloon by at least about 20% upon inflation compared to a balloon formed from an unstretched tube of identical composition.

19. The method of claim 18, wherein the extruded tube is longitudinally stretched at a forming temperature between about 0° and 90° C.

* * * * *

UNITED STATES PATENT AND TRADEMARK OFFICE
CERTIFICATE OF CORRECTION

PATENT NO. : 5,868,705
DATED : February 9, 1999
INVENTOR(S) : Celso J. Bagaoisan, et al It is certified that error appears in the above-indentified patent and that said Letters Patent is hereby corrected as shown below:

On the titel page, item [76], please add Mukund R. Patel, 427 Ridgefarm Drive, San Jose, CA 95123 add PERCUSURGE, INC., Sunnyvale, Calif., as the Assignee of the patent.

Signed and Sealed this

Twelfth Day of October, 1999

Attest:

Q. TODD DICKINSON

*Attesting Officer*    *Acting Commissioner of Patents and Trademarks*